US006824521B2

(12) United States Patent
Rich et al.

(10) Patent No.: US 6,824,521 B2
(45) Date of Patent: Nov. 30, 2004

(54) SENSING CATHETER SYSTEM AND METHOD OF FABRICATION

(75) Inventors: Collin A. Rich, Ypsilanti, MI (US); F. Randall Grimes, Ann Arbor, MI (US)

(73) Assignee: Integrated Sensing Systems, Inc., Ypsilanti, MI (US)

( * ) Notice: Subject to any disclaimer, the term of this patent is extended or adjusted under 35 U.S.C. 154(b) by 0 days.

(21) Appl. No.: 10/054,125

(22) Filed: Jan. 22, 2002

(65) Prior Publication Data

US 2002/0156417 A1 Oct. 24, 2002

Related U.S. Application Data

(60) Provisional application No. 60/278,634, filed on Mar. 26, 2001, and provisional application No. 60/263,327, filed on Jan. 22, 2001.

(51) Int. Cl.[7] .................................................. A61B 5/00
(52) U.S. Cl. ........................ 600/561; 600/300; 600/373
(58) Field of Search ................................ 600/300, 301, 600/344, 345–353, 359, 372–395, 486, 561, 585, 587; 607/122; 604/96.01, 264, 508, 523, 528

(56) References Cited

U.S. PATENT DOCUMENTS

| | | | | |
|---|---|---|---|---|
| 4,559,951 A | * | 12/1985 | Dahl et al. ................... | 600/374 |
| 4,592,364 A | | 6/1986 | Pinto | |
| 4,664,125 A | | 5/1987 | Pinto | |
| 4,685,469 A | * | 8/1987 | Keller ........................ | 600/488 |
| 4,858,615 A | | 8/1989 | Meinema | |
| 5,113,868 A | | 5/1992 | Wise et al. | |
| 5,207,103 A | * | 5/1993 | Wise et al. ................... | 73/724 |
| 5,509,424 A | | 4/1996 | Al-Ali | |
| 5,525,369 A | * | 6/1996 | Blackwell et al. ........... | 427/171 |
| 5,566,680 A | * | 10/1996 | Urion et al. ................. | 600/561 |
| 5,715,827 A | | 2/1998 | Corl et al. | |
| 5,813,996 A | * | 9/1998 | St. Germain et al. ........ | 600/585 |
| 5,902,248 A | | 5/1999 | Millar et al. | |
| 5,904,658 A | * | 5/1999 | Niederauer et al. ......... | 600/587 |
| 6,156,165 A | * | 12/2000 | Pierson et al. ........... | 204/192.12 |
| 6,264,612 B1 | * | 7/2001 | McConnell et al. ......... | 600/486 |

OTHER PUBLICATIONS

Mattox, Donald M. "Glossary of Terms & Acronyms Used in Surface Engineering" Handbook of Physical Vapor Deposition (PVD) Processing, 1998, Noyes Publications, pp. 799 & 896.*

Lai et al. "Chapter A: Wirebonding" http://extra.ivf.se/mgI/A–WireBonding/Chapter A1.htm#A1.1 Sep. 7, 2000.*

* cited by examiner

Primary Examiner—Mary Beth Jones
Assistant Examiner—Patricia C. Mallari
(74) Attorney, Agent, or Firm—Brinks Hofer Gilson & Lione (57) ABSTRACT

A microminiature sensing module and a sensing catheter system are provided. The module includes a sensor and signal conditioning circuit mounted on a substrate having electrical contacts positioned to facilitate connection of the module to an electrical bus, such as a dual lead electrical bus. The catheter system incorporates a dual lead electrical bus and one or more sensor modules. Methods of fabricating sensing catheter systems are also provided.

25 Claims, 6 Drawing Sheets

SENSING CATHETER SYSTEM AND METHOD OF FABRICATION

REFERENCE TO PREVIOUS APPLICATIONS

This application claims the benefit of U.S. Provisional Applications No. 60/263,327 filed on Jan. 22, 2001, and 60/278,634 filed on Mar. 26, 2001.

FIELD OF THE INVENTION

The present invention relates generally to the field of medical catheters and similar devices used to make internal measurements. More particularly, the invention relates to catheters that include microminiature sensors for detecting and/or measuring various physiological parameters.

BACKGROUND OF THE INVENTION

Catheters with integrated physiologic sensors have a variety of applications. For example, sensing catheters enable the measurement of various physiological parameters, such as blood pressure, blood flow, temperature, thermal gradients, and various chemistries. Due to their minimally invasive design, these catheters can measure these parameters at remote sites within a patient.

While a small circumference allows a catheter to enter and navigate through tight spaces, such as the vasculature and other body lumens, it also makes it difficult to add additional functionality to the catheter. For example, integration of physiological sensors into a catheter can prove difficult because the sensor must be integrated within the narrow spaces of the catheter. Also, any required electrical bus must be incorporated into the catheter. For example, U.S. Pat. No. 5,902,248 to Millar, et al. for a REDUCED SIZE CATHETER TIP MEASUREMENT DEVICE discloses a device that requires three leads for each sensor. Using this arrangement, the construction of a catheter with multiple sensors is difficult because numerous electrical leads must be packaged into the narrow geometries of the catheter. The use of an addressable electrical bus, such as that described in U.S. Pat. No. 5,113,868 to Wise, et al. for a ULTRAMINIATURE PRESSURE SENSOR WITH ADDRESSABLE READ-OUT CIRCUIT, reduces the need for multiple leads for each sensor.

Due to their relatively small size, microminiaturize sensors, also referred to as microsensors, microfabricated sensors, MEMS (micro electrical mechanical systems), and BioMEMS, provide excellent candidates for integration into catheter designs. However, even these small sensors have proven difficult to mechanically integrate into the relatively soft material of most catheters, such as plastics. Furthermore, even though microminiature sensors are relatively small, it is difficult to place these sensors in a specific location within a catheter during the manufacturing process. Also, it is often useful to include some type signal conditioning circuit with the sensor. Signal conditioning circuits modify or condition an output of the sensor such that it is in a form acceptable for use by an appropriate receiving and/or analyzing device. Ideally, the conditioning circuit is placed near the sensor to minimize noise effects on the raw sensor output signal. Thus, the conditioning circuit must also be placed within the catheter, which adds complexity to the manufacturing process.

Considering these and other drawbacks and difficulties, there is a need for a sensor module with an integrated signal conditioning circuit that facilitates catheter assembly. Also, there is a need for a sensing catheter system that includes an electrical bus that allows placement of multiple sensors in a catheter without necessitating multiple separate electrical leads for each sensor. Furthermore, there is a need for improved methods of fabricating sensing catheter systems.

SUMMARY OF THE INVENTION

The present invention provides a microminiature sensor module that includes a signal conditioning circuit and a physiological sensor. The module has electrical contacts that facilitate connection of the module to an electrical bus, such as within a sensing catheter.

The present invention also provides a sensing catheter system. In one embodiment, the system includes an electrical bus that provides electrical power and a signal return pathway to a microminiature sensor module. In one embodiment, the sensing catheter system comprises a catheter body having a circumferential wall and first and second lumens. The wall has at least one opening that exposes the second lumen. Two electrical leads are disposed in the second lumen, and can be used to provide electrical power and a return signal path. A microminiature sensor module is disposed in the opening and adjacent both of the electrical leads. Electrical contacts on the sensor module are in electrical communication with the two electrical leads. A sealant is disposed over the sensor module and fills the opening in the circumferential wall of the catheter body.

The present invention also provides methods of fabricating a sensing catheter system. A preferred method comprises forming a catheter body having a circumferential wall and first and second lumens, placing two electrical leads in the second lumen, forming an opening in the wall to expose the electrical leads, disposing a sensor module in the opening and adjacent the electrical leads, and placing the sensor module in electrical communication with the electrical leads. Lastly, the opening is sealed.

While the invention is defined by the claims appended hereto, additional understanding of the invention can be obtained by referencing the following description of preferred and alternate embodiments and the appended drawings.

DETAILED DESCRIPTION OF PREFERRED AND ALTERNATE EMBODIMENTS OF THE INVENTION

The following description of preferred embodiments and methods provides examples of the present invention. The embodiments discussed herein are merely exemplary in nature, and are not intended to limit the scope of the invention in any manner. Rather, the description of these preferred embodiments and methods serves to enable a person of ordinary skill in the relevant art to make, use and perform the present invention.

Figure 1:
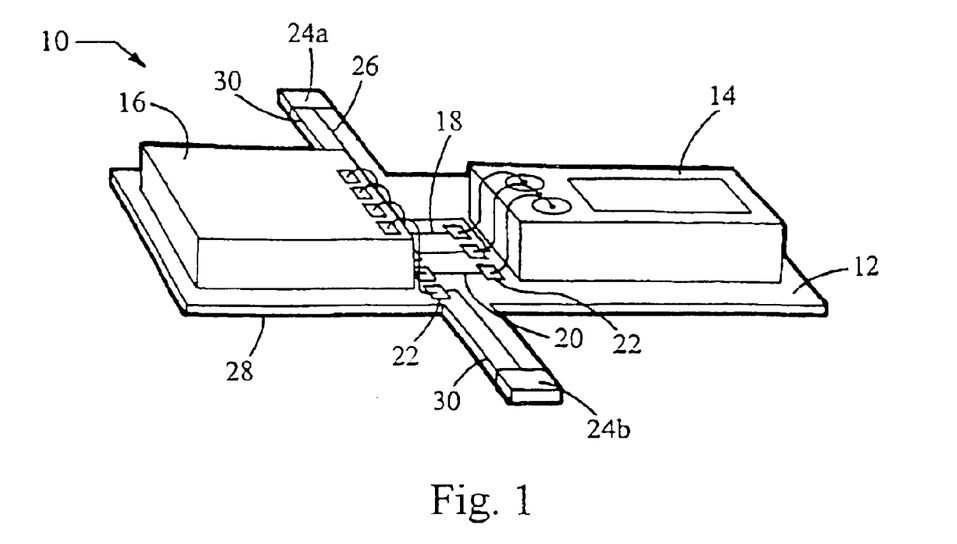
FIG. 1 is a perspective view of a microminiature sensor module according to a preferred embodiment of the present invention.

FIG. 1 illustrates a microminiature sensor module according to a preferred embodiment of the invention. As illustrated in the Figure, the module 10 preferably includes a substrate 12, a microminiature sensor 14, and a signal conditioning circuit 16. The sensor 14 and signal conditioning circuit 16 are disposed on the substrate 12. The substrate may be a separate element or an integral part of the sensor and/or circuit, or it may be optional if the sensor and circuit can be attached to each other without a substrate. The latter is the preferred method if space is limited in a given application.

The microminiature sensor 14 can be any suitable microminiature sensor adapted to detect and/or measure various physiological parameters. For example, the sensor 14 can comprise a pressure sensor, a temperature sensor, a flow sensor, a velocity sensor, or a sensor adapted to measure specific chemistries, such as gas content (e.g., $O_2$ and $CO_2$) and glucose levels. Various specific examples of these types of microminiature sensors are known to those skilled in the art, and any of these suitable sensors can be utilized in the sensor module of the present invention. While the specific type of sensor chosen will depend on the application of the catheter system, the sensor should be of a sufficiently small size in order to facilitate placement within a catheter according to the methods of the present invention.

The signal conditioning circuit 16 processes an output signal from the sensor 14 and prepares it for use by a receiving and/or analyzing device. For example, many systems receiving a pressure measurement as an input parameter prefer to receive the measurement output from a sensor in the form of a voltage, current, or frequency signal. Accordingly, the signal conditioning circuit 16 places the output signal of the sensor 14 into an appropriate form. Many different signal conditioning circuits are known to those skilled in the art, and any suitable circuit can be utilized. While the specific circuit chosen will depend upon the type of output signal needed in a particular sensing catheter system, the signal conditioning circuit should be of sufficiently small size to allow its placement in the sensor module of the present invention, and ultimately within the sensing catheter system according to the methods of the present invention.

Electrical connections 18 provide electrical communication between the sensor 14 and the signal conditioning circuit 16. The electrical connections 18 can be any suitable type of electrical connection, such as wirebonds between the sensor 14 and circuit 16. As illustrated in the Figure, the substrate 12 preferably includes circuit traces 20 and bond pads 22 that facilitate connection between the sensor 14 and circuit 16. Accordingly, in the preferred embodiment, the electrical connections 18 comprise a wirebond between the sensor 14 and a circuit trace 20 in the substrate, and a wirebond between the signal conditioning circuit 16 and the appropriate circuit trace 20 on the substrate 12. Other possible embodiments include using ball-bonds between pads on the substrate and pads on the sensor and/or circuit. Ultrasonic, laser, or a similar welding process could likewise be used to form the electrical connections. Conductive adhesives, such as conductive silver epoxy, could also be used to form the connections.

The microminiature sensor module 10 also preferably includes at least two electrical contacts 24 that enable connection of the module 10 to an electrical bus (not illustrated in FIG. 1). As illustrated in the Figure, the electrical contacts are preferably in electrical communication with the electrical connections 18 between the sensor 14 and the signal conditioning circuit 16. The use of two electrical contacts 24 allows the module 10 to be utilized with a dual lead electrical bus, such as the bus developed more fully below. However, it will be readily understood that any suitable number of electrical contacts can be employed. Also preferable, the electrical contacts 24 are arranged such that one electrical contact 24a lies at the beginning of an electrical path 26 that includes the sensor 14 and the signal conditioning circuit 16. The second electrical contact 24b preferably lies at the end of this path 26. Together, contacts 24a and 24b, and the associated leads and signal path, facilitate delivery of power to the sensor module from the receiving device, which also functions as a power supply. Furthermore, they provide a concurrent means of communication between the sensor module and the receiving device. In the preferred embodiment, modulation of the power supply current by the sensor module is the preferred method of transmitting the sensed data to the receiving device. Modulation of the supply voltage is the preferred method of controlling the sensor module. Other methods such as frequency modulation, pulse width modulation, and/or other means known to those familiar with the art may also be used.

FIG. 1 illustrates a preferred arrangement of the components of the sensor module 10. In this embodiment, the substrate 12 defines a main body region 28 that holds the sensor 14 and signal conditioning circuit 16. Also, the substrate 12 defines two opposing arms 30, each of which includes an electrical contact 24 at an end of the arm 30. The arms 30 are preferably centrally located on the body region 28. This arrangement facilitates connection of the module 10 to a dual lead electrical bus system, and allows for centralization of electrical connections 18 between the substrate 12, sensor 14, and signal conditioning circuit 16.

The substrate can be any substrate suitable for holding electrical componentry. Many examples of such substrates are known to those skilled in the art, and any can be used in the module. Furthermore, the substrate can be integrally formed with the sensor. The substrate can be either rigid or flexible. An example of a suitable rigid substrate includes a conventional printed circuit board, and an example of a suitable flexible substrate includes flexible circuit tape. Preferably, the substrate is flexible in order to facilitate movement (such as bending or twisting) of the module with a catheter body in which the module is incorporated.

Figure 2:
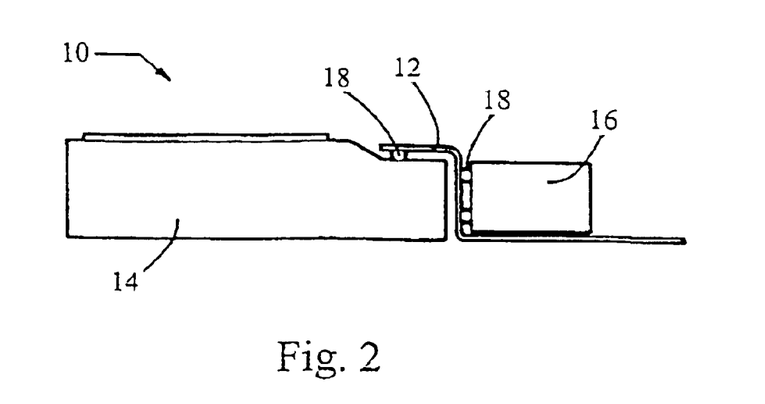
FIG. 2 is a side view of a microminiature sensor module according to an alternate embodiment of the present invention.

FIG. 1 illustrates a preferred embodiment in which both the sensor 14 and signal conditioning circuit 16 are both disposed on a top surface of the substrate 12. Various other types of arrangements can be utilized. For example, FIG. 2 illustrates an alternative embodiment in which the substrate 12 is attached to a top surface of the sensor 14 and a side surface of the signal conditioning circuit 16. It will be readily understood that, while the Figure illustrates the substrate attached to the top surface of the sensor and a side surface of the circuit, the substrate can be attached to any one surface of the sensor and any different corresponding surface of the signal conditioning circuit, as long as the necessary electrical connections can be made between the sensor and circuit. Furthermore, the sensor and circuit may be oriented in different directions, such as placing the circuit on its side, so long as the face of the sensor is not prevented from taking measurements. For example, the substrate can be attached to a side surface of the sensor and a top surface of the signal conditioning circuit. This arrangement may provide additional flexibility to the module 10.

Figure 3:
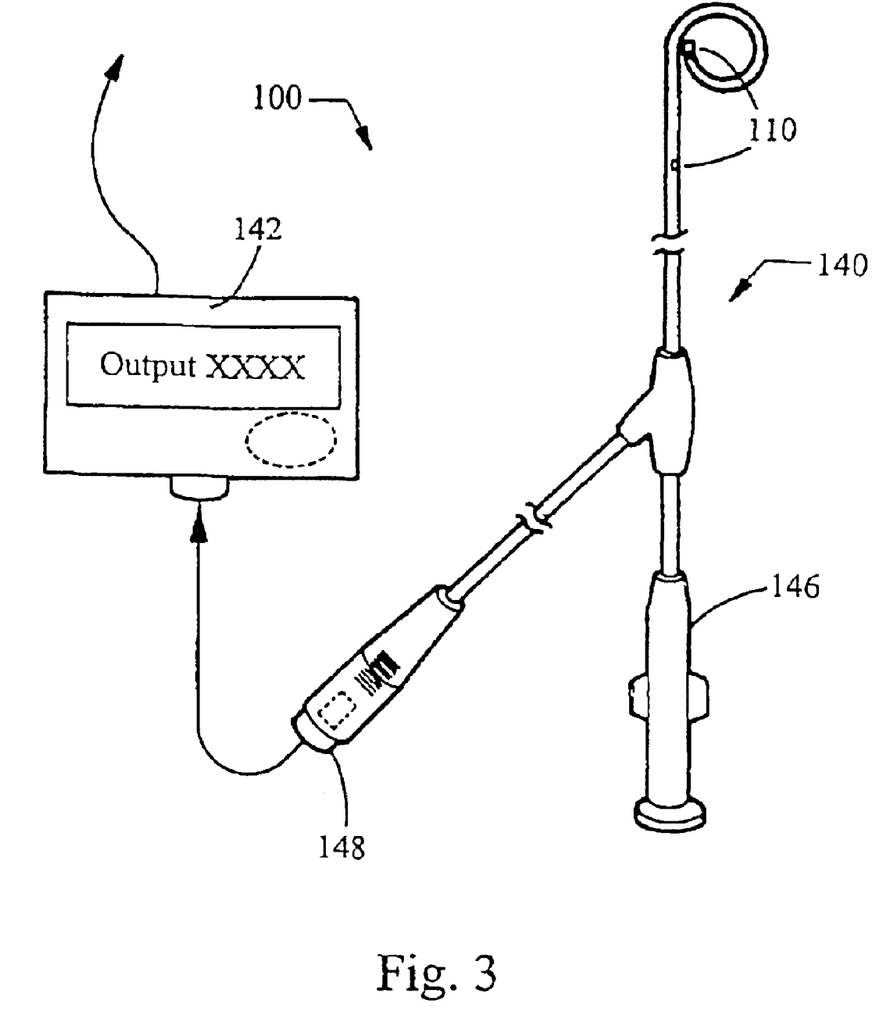
FIG. 3 is a perspective view of a sensing catheter system incorporating microminiature sensing modules.

FIG. 3 illustrates a sensing catheter system 100 according to the present invention. The catheter system includes a catheter 140 and a receiving and/or analyzing device 142. The catheter 140 includes a catheter body 144 and a luer assembly 146 for connection with a fluid manifold as typically used in a catheterization operation. A data output assembly 148 provides communication between sensor modules 110 and the receiving/analyzing device 142.

The catheter 140 can be any type of conventional catheter, including catheters having a single sheath as well as those having multiple sheaths. Furthermore, the catheter may include other conventional componentry, such as guidewires, stents, and balloons.

Figure 4:
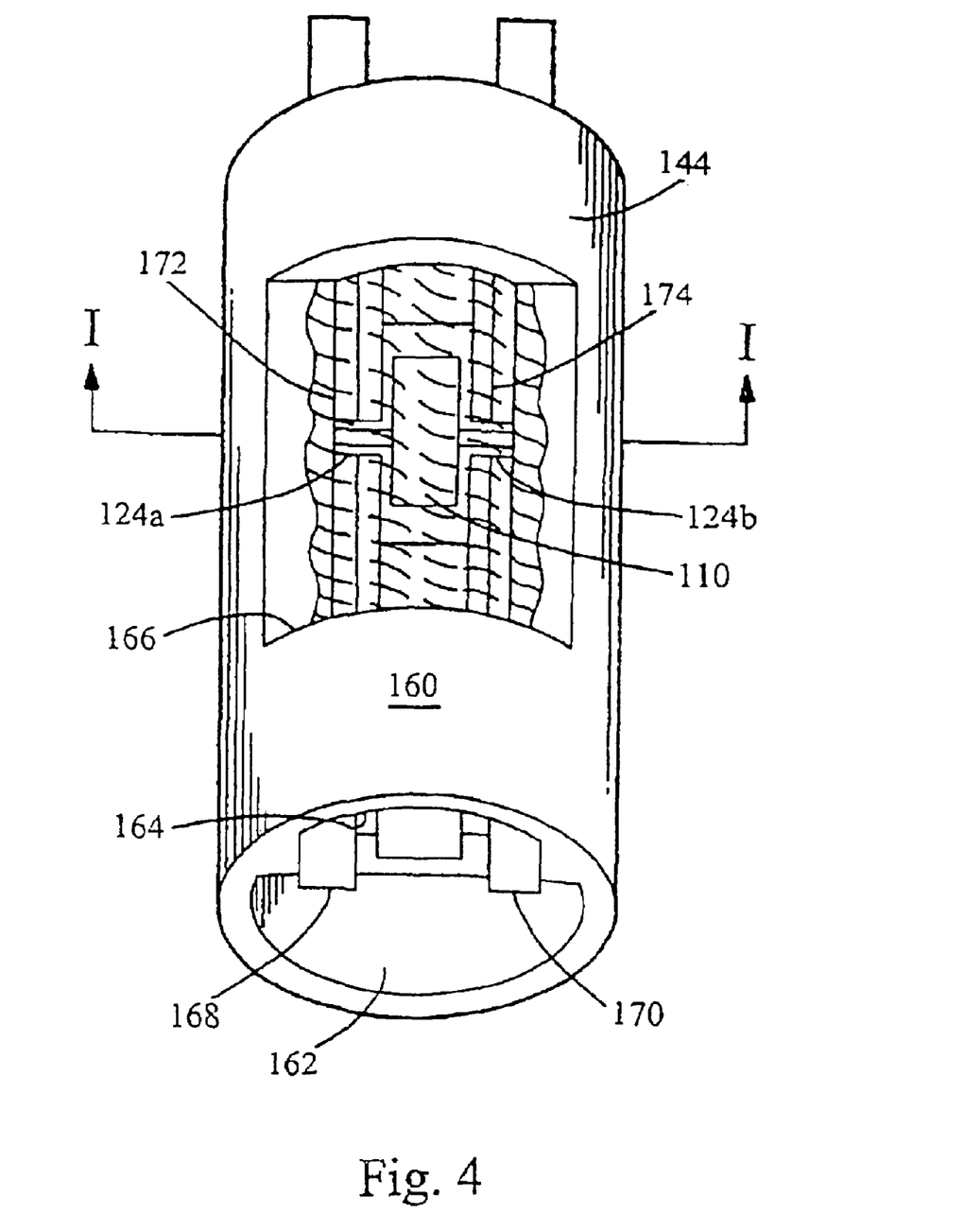
FIG. 4 is a perspective view of a segment of a sensing catheter system according to a preferred embodiment of the present invention.

The catheter body 144 houses the sensor modules 110 and the electrical bus that enables their operation. FIG. 4 illustrates a segment of the catheter body that includes an arrangement of the components according to a preferred embodiment of the invention. In this embodiment, the catheter body 144 has a circumferential wall and defines first 162 and second 164 lumens. The circumferential wall 160 defines an opening 166 to the second lumen 164.

First 168 and second 170 electrical leads are disposed in the second lumen 164. Preferably, as illustrated in the Figure, the first 168 and second 170 leads are spaced apart from each other and extend parallel to each other. Also preferable, the electrical leads 168, 170 are ribbon forms of a suitable conductive material such as copper, with suitable insulation, such as varnish, to prevent shorting to each other. At some point along the length of the catheter, one or both of the leads may be woven into the peripheral braid of a braided catheter body. The catheter braid may serve as one of the leads. The catheter braid may also be used as a ground shield to reduce electrical noise in the leads.

The sensing catheter 100 also includes one or more microminiature sensor module 110 according to the present invention. The sensor module 110 is disposed in the opening 166 in the circumferential wall 160. Also, the module 110 lies adjacent the first 168 and second 170 electrical leads.

First 172 and second 174 electrical connections provide electrical communication between the first 168 and second 170 electrical leads and the first 124a and second 124b electrical contacts of the sensor module 110.

The use of dual electrical leads provides an electrical bus system to which sensor modules 110 can be easily connected. Furthermore, as illustrated in FIG. 4, the electrical leads 168, 170 preferably extend beyond the length of the opening 166. This arrangement allows placement of the sensor module 110 at any point along the leads 168, 170 within the opening 166. Also, if the opening 166 is sufficiently large, multiple modules 110 can be placed along the leads 168, 170 within the opening. Alternatively, multiple openings 166 may be placed in the catheter at various locations to facilitate multiple sensor modules.

Figure 5:
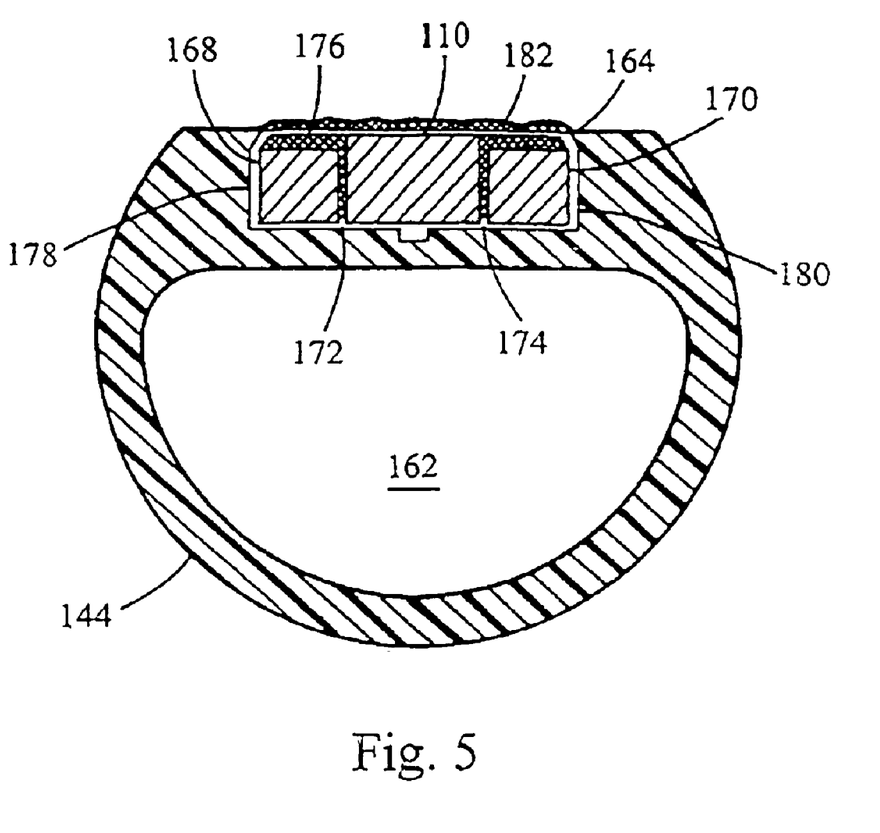
FIG. 5 is a cross-sectional view taken along line I—I in FIG. 4 illustrating a preferred arrangement of a microminiature sensor module and electrical leads within a catheter body.

The sensor module 110 and leads 168, 170 can be arranged in any manner that establishes the necessary electrical communication between the leads 168, 170 and the module 110. FIG. 5 illustrates a preferred arrangement of the module 110 and leads 168, 170 within the catheter body 144. In this embodiment, the sensor module 110 is disposed between the electrical leads 168, 170. Also, a retaining member 176, such as a unshaped clip, is disposed over the sensor module 110 and engages the leads 168, 170 to form the electrical connections 172, 174 as electrical compression bonds.

Preferably, the catheter body 144 defines first 178 and second 180 shoulder regions. A sealant 182 is disposed over the components to fill the opening 166. Preferably, when shoulders 178, 180 are present, the sealant 182 extends into the shoulders 178, 180, facilitating retention of the module 110 in the opening 166.

Figure 6:
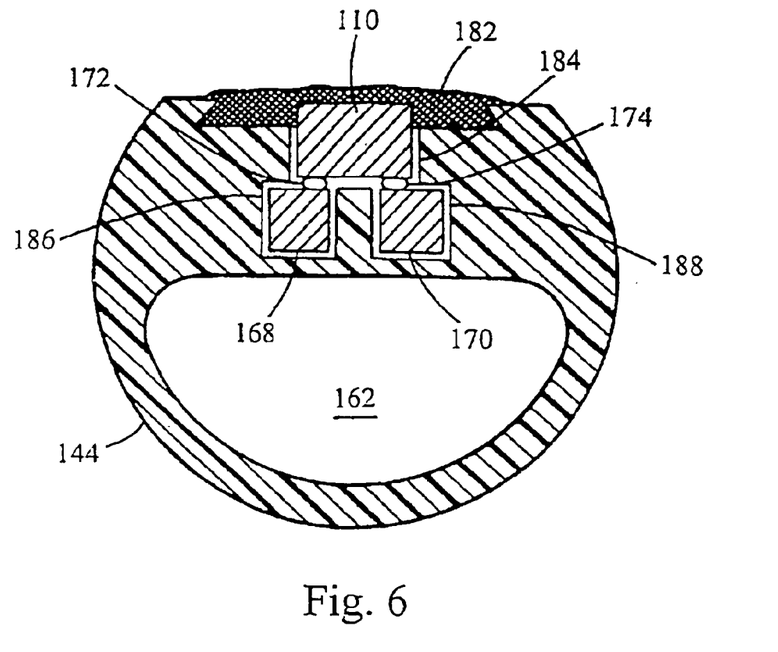
FIG. 6 illustrates a first alternative arrangement of a microminiature sensor module and electrical leads within a catheter body.

FIG. 6 illustrates an alternative arrangement of the components within the catheter body 144. In this embodiment, the second lumen 164 comprises a main channel portion 184 and first 186 and second 188 sub channels. Preferably, the sub channels 186, 188 lie below the main channel 184. The electrical leads 168, 170 are individually disposed in the first 186 and second 188 sub channels. Also, the sensor module 110 is disposed in the main channel 184. In this embodiment, electrical connections 172, 174 preferably comprise ball bonds disposed between the sensor module 110 and the electrical leads 168, 170.

Figure 7:
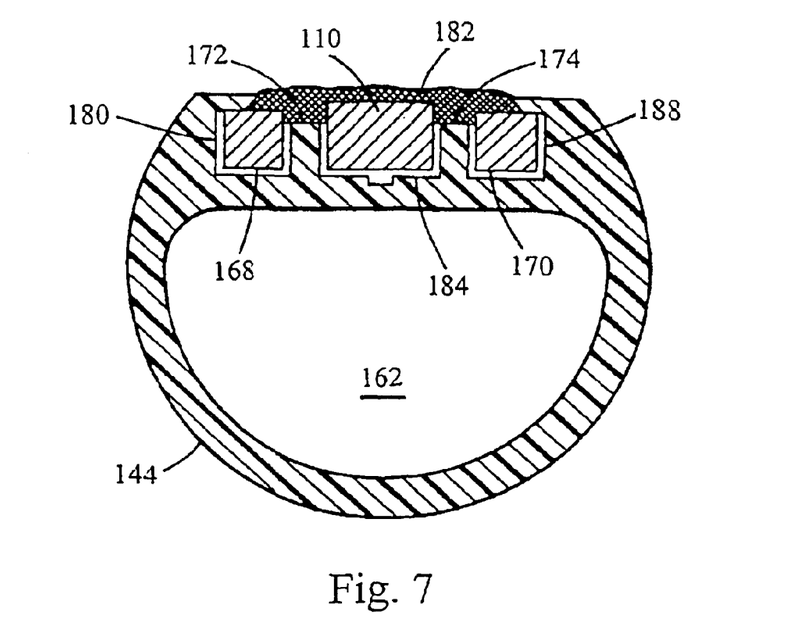
FIG. 7 is a second alternative arrangement of a microminiature sensor module and electrical leads within a catheter body.

FIG. 7 illustrates a second alternative arrangement of the components within the catheter body 144. In this embodiment, the second lumen 164 comprises main 184 and sub 186, 188 channels, as in the first alternative arrangement illustrated in FIG. 6. In this embodiment, however, the sub channels 186, 188 are disposed laterally from the main channel 184. Similar to the first alternative arrangement, the electrical leads 168, 170 are disposed within the sub channels 186, 188 and the sensor module 110 is disposed within the main channel 184. Electrical connections 172, 174 in this embodiment comprise wirebonds. To facilitate the connection of wirebonds to the components, the first 168 and second 170 electrical leads preferably each have at least one flat surface for attachment of the wirebond. Accordingly, suitable cross-sectional shapes for the electrical leads 168, 170 include square, rectangular, and half circle shapes.

Figure 8:
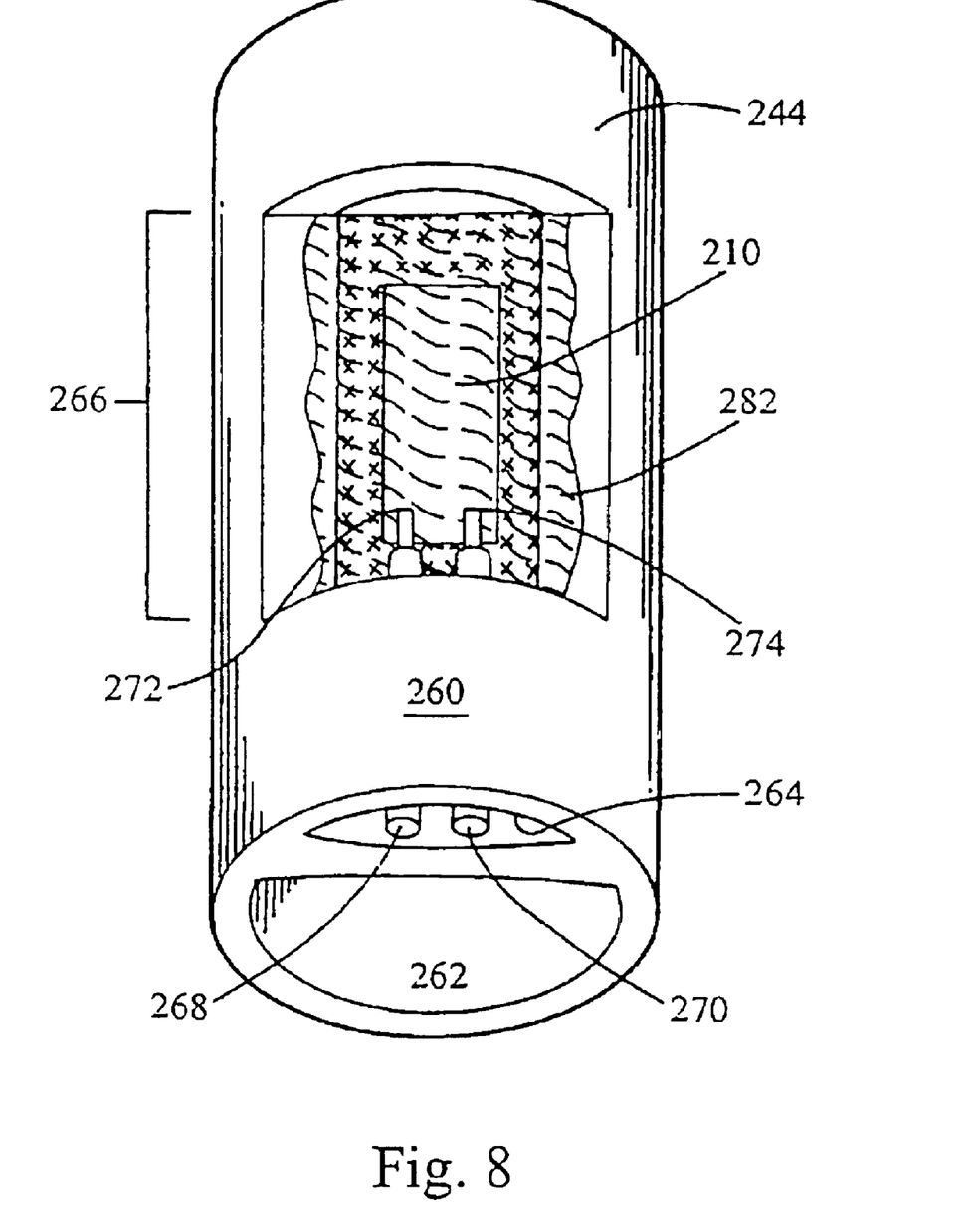
FIG. 8 is a perspective view of a segment of a sensing catheter system according to an alternative embodiment of the present invention.

FIG. 8 illustrates an alternative embodiment of the sensing catheter. In this embodiment, like reference numbers refer to similar features and/or components illustrated above for the preferred embodiment.

In this embodiment, the electrical leads 268, 270 comprise conventional wires threaded through the second lumen 264. The wires terminate at a point at which the sensor module 210 is disposed in the opening 266. Solder joints form the electrical connections 272, 274 between the leads 268, 270 and the sensor module 210. Ultrasonic, laser, or a similar welding process could likewise be used to form the electrical connections. Conductive adhesives, such as conductive silver epoxy, could also be used. Furthermore, slots may be included in the substrate to aid the proper alignment of leads 268, 270.

The present invention also provides methods of fabricating a sensing catheter assembly. A preferred method according to the present invention comprises forming a catheter body having a circumferential wall and defining first and second lumens. Next, two electrical leads are disposed within the second lumen to form an electrical bus for connection to a microminiature sensor module. The electrical leads can be disposed in the second lumen by either threading wires or ribbons through the lumen, or by forming the leads at that time of forming the catheter body. For example, the electrical leads can be co-extruded with the catheter body using an appropriate extruder.

The method also includes forming an opening in the circumferential wall of the catheter body such that the second lumen is exposed. When the electrical leads are contained within the second lumen, the opening also exposes the electrical leads. A microminiature sensor module according to the present invention is provided, and is disposed in the opening in the circumferential wall of the catheter body. The sensor module is disposed adjacent each of the electrical leads in order to facilitate connections. Next, the electrical contacts of the sensor module are placed in electrical communication with the electrical leads. Lastly, the opening is sealed with an appropriate material, such as an encapsulation or potting material.

When forming the electrical connections between the sensor module and the leads, any suitable connection method can be utilized. For example, a retaining member, such as a compressive clip, can be positioned adjacent the sensor module and the leads such that an electrical compression bond is formed between the components. Furthermore, ball bonds, wirebonds, or other suitable electrical bonds can be formed between the sensor module and each of the electrical leads.

The references cited in this disclosure, except to the extent they contradict any statement or definition made herein, are hereby incorporated by reference in their entirety.

The foregoing disclosure includes the best mode devised by the inventors for practicing the invention. It is apparent, however, that several variations in the apparatuses and methods of the present invention may be conceivable by one skilled in the art. Inasmuch as the foregoing disclosure is intended to enable one skilled in the pertinent art to practice the instant invention, it should not be construed to be limited thereby, but should be construed to include such aforementioned variations.

We claim:

1. A method of fabricating a sensing catheter assembly, comprising:
   forming a catheter body having a circumferential wall and defining first and second lumens,
   placing first and second electrical leads in the second lumen by co-extruding the first and second electrical leads and the catheter body;
   forming an opening in the circumferential wall to expose the first and second electrical leads;
   providing a microminiature sensor module comprising a substrate, a microminiature sensor disposed on the substrate, a signal conditioning circuit disposed on the substrate and in electrical communication with the sensor, and first and second electrical contacts in electrical communication with the sensor and circuit;
   disposing the sensor module in the opening and adjacent the first and second electrical leads;
   placing the first and second electrical contacts in electrical communication with the first and second electrical leads; and
   sealing the opening.

2. The method of claim 1, wherein placing the first and second electrical contacts in electrical communication with the first and second electrical leads comprises positioning a retaining member adjacent the sensor module and first and second electrical leads.

3. The method of claim 1, wherein placing the first and second electrical contacts in electrical communication with the first and second electrical leads comprises forming a ball bond between the sensor module and each of the first and second electrical leads.

4. The method of claim 1, wherein placing the first and second electrical contacts in electrical communication with the first and second electrical leads comprises forming a wire bond between the sensor module and each of the first and second electrical leads.

5. The method of claim 1, wherein placing the first and second electrical contacts in electrical communication with the first and second electrical leads comprises forming a weld joint between the sensor module and each of the first and second electrical leads.

6. The method of claim 1, wherein placing the first and second electrical contacts in electrical communication with the first and second electrical leads comprises forming a solder joint between the sensor module and each of the first and second electrical leads.

7. The method of claim 1, wherein placing the first and second electrical contacts in electrical communication with the first and second electrical leads comprises forming a conductive adhesive joint between the sensor module and each of the first and second electrical leads.

8. A sensing catheter system comprising:
   a catheter body having a circumferential wall and defining first and second lumens, the circumferential wall defining at least one opening to the second lumen;
   first and second electrical leads disposed in the second lumen;
   a microminiature sensor module disposed in the opening in the circumferential wall and adjacent the first and second electrical leads, the sensor module comprising a substrate, a microminiature sensor and a signal conditioning circuit disposed on the substrate, and first and second electrical contacts in electrical communication with the sensor and circuit;
   first and second electrical connections between the first and second electrical leads and the first and second electrical contacts;
   sealant disposed over the sensor module and filling the opening in the circumferential wall; and
   a second sealant disposed over the sealant.

9. The sensing catheter system of claim 8, wherein the at least one opening comprises a plurality of spaced-apart openings in the circumferential wall; and
   wherein a microminiature sensor module is disposed in each of the plurality of openings.

10. The sensing catheter system of claim 8, wherein the sensor module is disposed between the first and second electrical leads.

11. The sensing catheter system of claim 10, further comprising a retaining member disposed in the second lumen and engaged with the first and second electrical leads to form the first and second electrical connections as electrical compression bonds.

12. The sensing catheter system of claim 11, wherein the retaining member comprises a u-shaped clip.

13. The sensing catheter system of claim 8, wherein the substrate defines a body region and two opposing arms; and
   wherein each electrical contact is disposed at an end of an arm away from the body region of the substrate.

14. The sensing catheter system of claim 8, wherein the first and second electrical leads comprise ribbons.

15. The sensing catheter system of claim 8, wherein the first and second electrical leads comprise wires.

16. The sensing catheter system of claim 15, wherein the wires are shielded wires.

17. A sensing catheter system, comprising:
   a catheter body having a circumferential wall and defining first and second lumens, the circumferential wall defining at least one opening to the second lumen, the second lumen including a main channel portion and first and second sub-channel portions;

first and second electrical leads disposed in the second lumen;

a microminiature sensor module disposed in the opening in the circumferential wall and adjacent the first and second electrical leads, the sensor module comprising a substrate, a microminiature sensor and a signal conditioning circuit disposed on the substrate, and first and second electrical contacts in electrical communication with the sensor and circuit;

first and second electrical connections between the first and second electrical leads and the first and second electrical contacts; and sealant disposed over the sensor module and filling the opening in the circumferential wall.

18. The sensing catheter system of claim 17, wherein the first and second electrical leads are individually disposed in the first and second sub-channel portions and the sensor module is disposed in the main channel portion.

19. The sensing catheter system of claim 18, wherein the first and second electrical connections comprise ball bonds disposed between the sensor module and the first and second electrical leads.

20. The sensing catheter system of claim 18, wherein the first and second electrical connections comprise wire bonds.

21. The sensing catheter system of claim 20, wherein the first and second electrical leads each have at least one flat surface and the wire bond is attached to the at least one flat surface.

22. The sensing catheter system of claim 18, wherein the first and second electrical connections comprise solder joints.

23. The sensing catheter system of claim 18, wherein the first and second electrical connections comprise weld joints.

24. The sensing catheter system of claim 18, wherein the first and second electrical connections comprise conductive adhesive joints.

25. A sensing catheter system, comprising:

a catheter body having a circumferential wall and defining a first lumen and a second lumen having first and second shoulder regions, the circumferential wall defining at least one opening to the second lumen;

first and second electrical leads disposed in the second lumen;

a microminiature sensor module disposed in the opening in the circumferential wall and adjacent the first and second electrical leads, the, sensor module comprising a substrate, a microminiature sensor and a signal conditioning circuit disposed on the substrate, and first and second electrical contacts in electrical communication with the sensor and circuit;

a u-shaped retaining member disposed in the second lumen and engaged with the first and second electrical leads to place the first and second electrical leads in electrical communication with the first and second electrical contacts; and sealant disposed over the sensor module, extending into the first and second shoulder regions, and filling the opening in the circumferential wall.

* * * * *